United States Patent [19]
McDevitt et al.

[11] Patent Number: 5,814,071
[45] Date of Patent: Sep. 29, 1998

[54] SUTURE ANCHOR ASSEMBLY AND METHODS

[75] Inventors: Dennis McDevitt, Upton; John Rice, Lincoln, both of Mass.

[73] Assignee: Innovasive Devices, Inc., Marlborough, Mass.

[21] Appl. No.: 719,659

[22] Filed: Sep. 25, 1996

Related U.S. Application Data

[63] Continuation-in-part of Ser. No. 337,944, Nov. 10, 1994, Pat. No. 5,649,963, Ser. No. 568,348, Dec. 6, 1995, and Ser. No. 574,463, Dec. 7, 1995, Pat. No. 5,643,321.

[51] Int. Cl.⁶ .................................................. A61B 17/04
[52] U.S. Cl. ............................................ 606/232; 606/144
[58] Field of Search ............................... 606/232, 72, 74, 606/144, 143, 147, 145

[56] References Cited

U.S. PATENT DOCUMENTS

| | | |
|---|---|---|
| Re. 34,293 | 6/1993 | Goble et al. . |
| 2,381,050 | 8/1945 | Hardinge . |
| 3,036,482 | 5/1962 | Kenworthy et al. . |
| 3,566,739 | 3/1971 | Lebar . |
| 3,708,883 | 1/1973 | Flander . |
| 3,842,824 | 10/1974 | Neufeld . |
| 4,013,071 | 3/1977 | Rosenberg . |
| 4,091,806 | 5/1978 | Aginsky . |
| 4,408,938 | 10/1983 | Maguire . |
| 4,484,570 | 11/1984 | Sutter . |
| 4,492,226 | 1/1985 | Belykh et al. . |
| 4,506,670 | 3/1985 | Crossley . |
| 4,590,928 | 5/1986 | Hunt et al. . |

(List continued on next page.)

FOREIGN PATENT DOCUMENTS

| | | |
|---|---|---|
| 0 058 744 | 9/1982 | European Pat. Off. . |
| 0 124 489 | 11/1984 | European Pat. Off. . |
| 0 232 049 | 8/1987 | European Pat. Off. . |
| 0 241 240 | 10/1987 | European Pat. Off. . |
| 87302940 | 10/1987 | European Pat. Off. . |
| 0 260 970 | 3/1988 | European Pat. Off. . |
| 0 270 704 | 6/1988 | European Pat. Off. . |
| 86117360 | 6/1988 | European Pat. Off. . |
| 0251583 | 7/1988 | European Pat. Off. . |
| 0 340 159 | 11/1989 | European Pat. Off. . |
| 0 409 364 | 1/1991 | European Pat. Off. . |
| 0 574 707 | 12/1993 | European Pat. Off. . |
| 2054731 | 5/1971 | France . |
| 2 346 591 | 10/1977 | France . |
| 2 622 430 | 5/1989 | France . |
| 90250174 | 5/1989 | France . |
| 3406961 | 9/1985 | Germany . |
| 85 20206 | 6/1986 | Germany . |
| 2 084 468 | 4/1982 | United Kingdom . |
| 88/09157 | 12/1988 | WIPO . |
| 89/01767 | 3/1989 | WIPO . |
| PCT/US91/ 07003 | 9/1991 | WIPO . |
| PCT/US94/ 13954 | 12/1994 | WIPO . |

*Primary Examiner*—Michael Powell Buiz
*Assistant Examiner*—Kevin Truong
*Attorney, Agent, or Firm*—Choate, Hall & Stewart

[57] ABSTRACT

A suture anchor assembly is described which includes an elongated insertion stem and an approximately cylindrical anchoring element having an axial channel for receiving the insertion stem. In its nonexpanded state, the anchoring element can be placed into a pre-drilled opening in a bone. An expander element loaded onto the insertion stem is engaged with a proximal end of the anchoring element. The proximal end of the anchoring element is capable of telescoping or camming movement over the distal end of the expander element so that resilient proximal portions of the anchoring element are forced outward against the expander element, causing the resilient proximal portions of the anchoring element to expand into the bone hole, fixing the anchoring element in a pressure fit firmly within the opening. A kit for emplacing and removing the suture anchor is also provided as well as methods for attaching a suture to a bone using the present assembly.

32 Claims, 18 Drawing Sheets

U.S. PATENT DOCUMENTS

| | | |
|---|---|---|
| 4,632,100 | 12/1986 | Somers et al. . |
| 4,716,893 | 1/1988 | Fischer et al. . |
| 4,741,330 | 5/1988 | Hayhurst . |
| 4,778,468 | 10/1988 | Hunt et al. . |
| 4,871,289 | 10/1989 | Choiniere . |
| 4,873,976 | 10/1989 | Schreiber . |
| 4,927,421 | 5/1990 | Goble . |
| 4,940,467 | 7/1990 | Tronzo . |
| 4,944,742 | 7/1990 | Clemow et al. . |
| 5,013,316 | 5/1991 | Goble et al. . |
| 5,037,422 | 8/1991 | Hayhurst et al. . |
| 5,046,513 | 9/1991 | Gatturna et al. . |
| 5,116,337 | 5/1992 | Johnson . |
| 5,141,373 | 8/1992 | Kendall . |
| 5,141,520 | 8/1992 | Goble et al. . |
| 5,152,763 | 10/1992 | Johnson . |
| 5,169,400 | 12/1992 | Murling . |
| 5,176,682 | 1/1993 | Chow . |
| 5,207,679 | 5/1993 | Li . |
| 5,209,753 | 5/1993 | Biedermann et al. . |
| 5,224,946 | 7/1993 | Hyhurst et al. . |
| 5,236,445 | 8/1993 | Hayhurst et al. . |
| 5,248,231 | 9/1993 | Denham et al. . |
| 5,258,015 | 11/1993 | Li et al. . |
| 5,268,001 | 12/1993 | Nicholson et al. . |
| 5,324,308 | 6/1994 | Pierce . |
| 5,326,205 | 7/1994 | Anspach, Jr. et al. . |
| 5,354,298 | 10/1994 | Lee et al. . |
| 5,411,523 | 5/1995 | Goble . |
| 5,417,712 | 5/1995 | Whittaker et al. . |
| 5,458,601 | 10/1995 | Young, Jr. et al. . |
| 5,464,427 | 11/1995 | Curtis et al. . |
| 5,472,452 | 12/1995 | Trott . |
| 5,480,403 | 1/1996 | Lee et al. . |
| 5,486,197 | 1/1996 | Le et al. . |
| 5,489,210 | 2/1996 | Hanosh . |
| 5,496,326 | 3/1996 | Johnson . |
| 5,501,683 | 3/1996 | Trott . |
| 5,501,695 | 3/1996 | Anspach et al. . |
| 5,522,845 | 6/1996 | Wenstrom, Jr. . |
| 5,545,180 | 8/1996 | Le et al. . |
| 5,571,104 | 11/1996 | Li . |
| 5,626,614 | 5/1997 | Hart ........ 606/232 |
| 5,649,963 | 7/1997 | McDevitt ........ 606/232 |

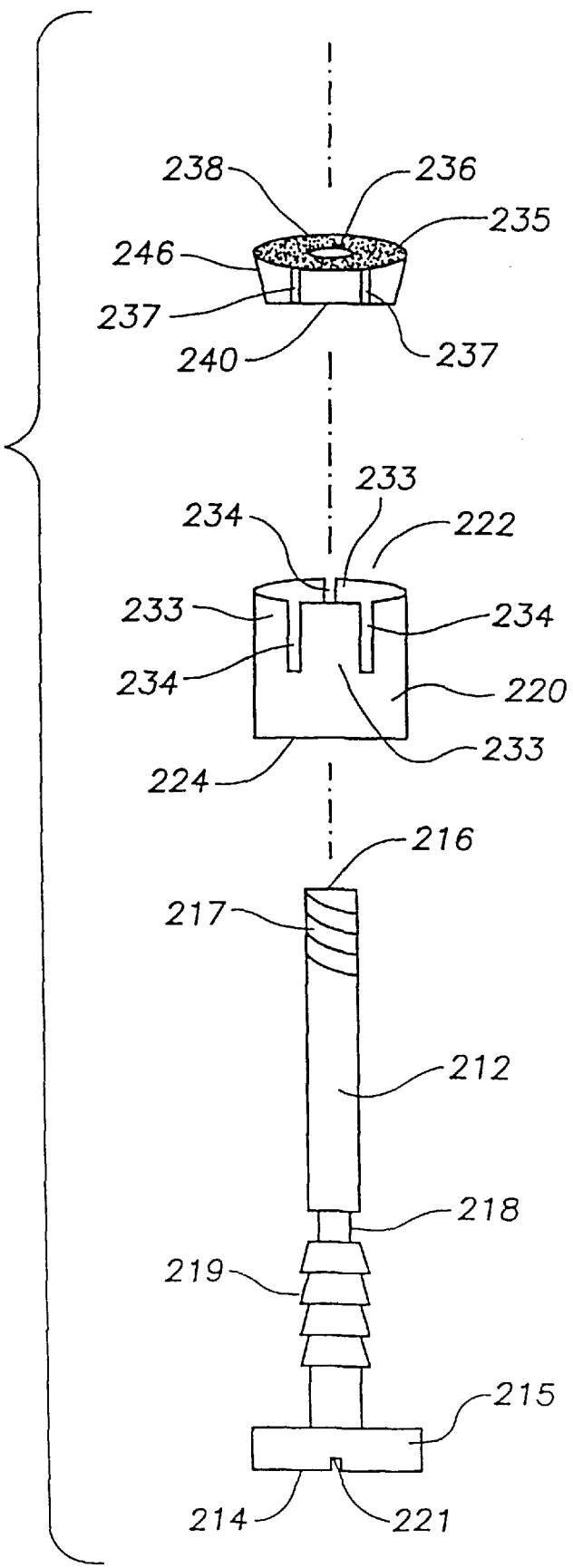

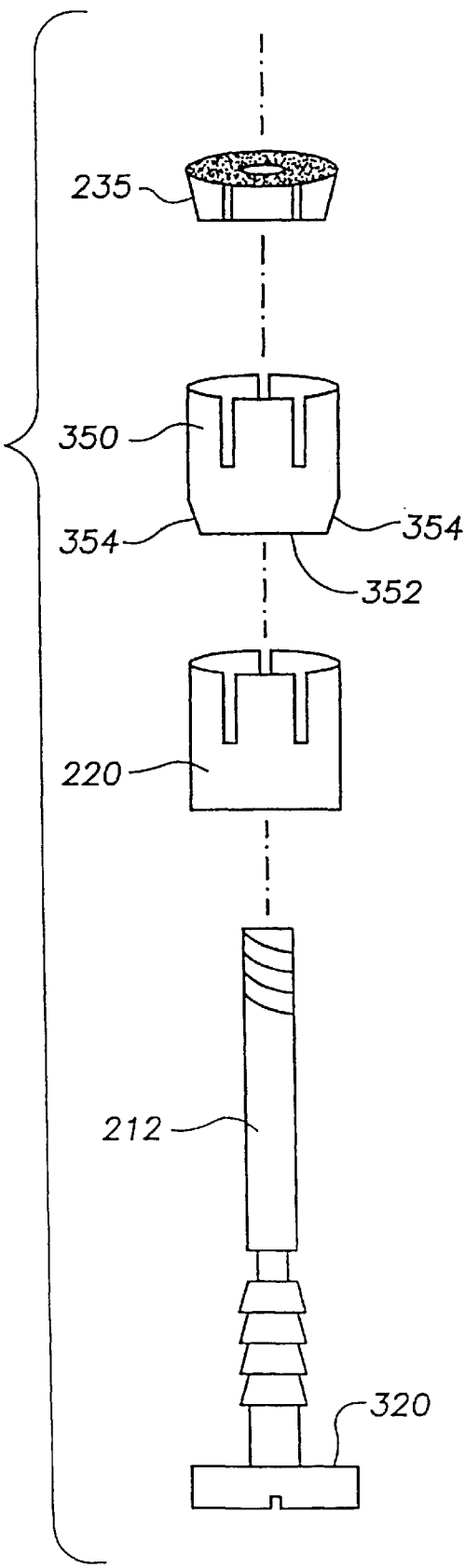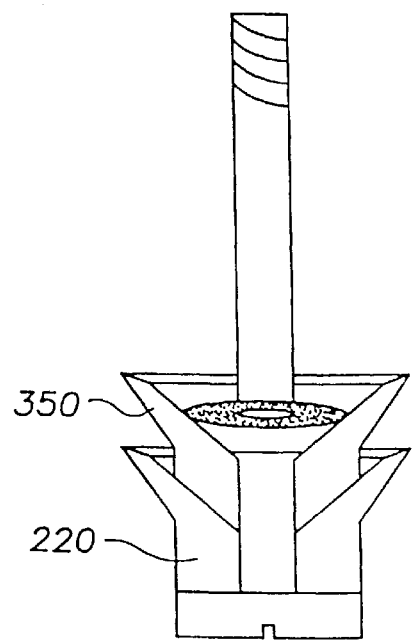

SUTURE ANCHOR ASSEMBLY AND METHODS

This application is a continuation in part of commonly assigned U.S. patent application Ser. No. 08/337,944, filed Nov. 10, 1994 U.S. Pat. No. 5,649,963, the teachings of which are incorporated herein by reference. This application is also a continuation in part of U.S. patent application Ser. No. 08/568,348, filed Dec. 6, 1995, and of U.S. patent application Ser. No. 08/574,463, filed Dec. 7, 1995, U.S. Pat. No. 5,643,321 of which are incorporated herein by reference.

A variety of techniques are available for affixing objects such as soft tissue to bone. The oldest technique utilizes thread passed through the bone and the tissue to sew the tissue down to the bone. Many sizes, shapes and types of suture and suture needles are available to accomplish this task. Today, this method is still used for repair of tendons and ligaments in older osteoarthritic patients, although passing a suture through bone is generally difficult and tedious.

Soft tissue repairs also have been accomplished with metal screws or staples that attach soft tissue to bone. Metal screws and/or staples are, however, subject to corrosion and consequent loss of structure. Moreover, the presence of metal in an anatomical site can interfere with imaging and diagnostic or therapeutic treatments near the site. For example, any metal implants may have to be removed by surgery prior to magnetic resonance imaging. Patient sensitivity to nickel ions and stainless steel implants has fueled a growing controversy regarding the use of materials containing high quantities of nickel including nickel-titanium alloys such as Nitinol. Also, it is almost impossible to adjust the compression exerted by screws and staples on soft tissue. Thus, these devices are not fully satisfactory for soft tissue repair.

Other devices employ a suture anchor installation affixed to an arc of wire or a plurality of barbs disposed on an outer surface of the suture anchor body. The barbs or arc of wire are set into a bone by applying traction to the suture. Unfortunately, it is not always possible to position the anchor at a precise location within a bone if an anchor is being drawn upwards in a bone hole by applying tension to a suture. Furthermore, many of the fastening devices require some type of impact or impulse to set the fastener in position. Impact emplacement or setting of bone/suture anchors may result in injury to the patient as well as placing unnecessary strain on the bone/suture fastener itself. This is especially problematic when suture anchors are intended to be placed in soft bone such as in procedures to repair anterior cruciate ligaments or repair torn rotator cuffs.

SUMMARY OF THE INVENTION

One embodiment of the invention is an anchoring device to affix a suture in a bone. The suture anchor includes an expander element having proximal and distal ends, the distal end for engagement with a proximal end of an anchoring element. The anchor also includes an anchoring element for insertion into a bone hole, the element being adapted for movement within the bone hole from a first position, where a proximal end of the insertion element is in facing relationship to the distal end of the expander element, to a second position, where the anchoring element moves proximally within the bone hole so that its proximal end telescopes over the distal end of the expander element, forcing the proximal end of the anchoring element into a wall of the bone hole. The anchor further includes means for moving the anchoring element from the first to the second position.

In a further embodiment, the device includes a tubular anchoring element for engagement with a hole drilled in a bone that has opposed proximal and distal ends connected by way of a central longitudinal axis. The element has defined between the ends an axial channel extending from the proximal end of the element to the distal end of the element and having inner and outer peripheral surfaces forming a wall between the surfaces. The wall further has defined in it a series of axially-oriented slots beginning at the proximal end and extending distally. A suture retainer is engaged with the anchoring element. The anchoring element further includes a plurality of wall sections that are defined between the axially-oriented slots. Proximal ends of the wall sections include a first camming surface for mating with another camming surface on an expander element so that the first camming surface is arranged for telescoping movement over the other camming surface to expand the wall sections into the bone.

The invention also encompasses an anchoring device to affix a suture in a bone that includes a tubular anchoring element having opposed proximal and distal ends and an axial channel extending from the proximal end of the element to the distal end of the element. The anchoring element has several flexible wall sections that are adapted for movement from a first position, where the flexible wall sections are arranged along the outer peripheral surface of the element, to a second position, where proximal ends of the flexible wall sections are forced to obliquely expand outwardly into a wall of the bone hole. A suture retainer is also engaged with the element. Preferably, the wall sections are more flexible at their respective proximal ends than at their respective distal ends. Other embodiments of the anchoring element include those having screw threads disposed on the distal end at an inner peripheral surface.

The invention also pertains to a suture anchor assembly. The assembly includes an insertion stem having proximal and distal ends, the distal end for engagement with a distal end of a tubular anchoring element; a tubular anchoring element of the invention; and a tubular expander element having an axial channel defined between the proximal and distal ends. The expander element is adapted for loading onto the stem and has a distal end designed to engage with the proximal end of the tubular anchor element. The anchor element is adapted for movement from a first position, where its proximal end is engaged with the distal end of the expander element, to a second position, so that the tubular anchor element telescopes over the distal end of the expander element and the flexible wall sections of the anchoring element expand into a wall of the bone hole.

Most preferably, the insertion stem includes a frangible section adjacent to its distal end and designed to break when sufficient tension is applied to the stem The proximal end of the expander element may include a peripheral flange integral with the proximal end. Included at the distal end of the expander and the proximal end of the flexible wall sections are camming surfaces adapted to engage with each other in order to expand the wall sections into the bone.

The preferred assembly of the invention also includes a tool for removing the anchor element once the anchor element is deployed in bone hole and a tool for applying tension to the insertion stem.

A kit for deploying a suture anchor in a bone hole includes the suture anchor assembly of the invention, a drill, a drill guide, a deployment device, and a tool for removing the anchor element once deployed.

Methods for deploying a suture anchor in a bone hole are described and include providing an anchoring element of the invention for insertion into an opening in a bone and engaging the anchoring element with an insertion stem. Next, an expander element is engaged with the insertion stem so that a distal end of the expander element is engaged with a proximal end of the anchoring element. The insertion stem with its loaded anchoring element is placed into the bone hole and the expander element is fixed in position in the bone hole. A tensional force is applied to the insertion stem so that the proximal end of the anchoring element telescopes over the distal end of the expander element and an outer surface of the anchoring element engages with the bone. The insertion stem is then released from the anchoring element. Most preferably, the step of releasing includes activating a frangible section of the insertion stem so that it breaks.

It is an object of the present invention to provide a suture anchor of simple design and construction.

It is another object of the present invention to provide a suture anchor having one or more bioabsorbable components.

It is yet another object of the present invention to provide an apparatus for emplacing a suture anchor in a bone that does not require an impact or impulse in order to deploy the anchor.

It is another object of the present invention to provide a method for emplacing a suture anchor that can be used in soft bone and can be removed from the soft bone after deployment.

BRIEF DESCRIPTION OF THE DRAWINGS

The following description of the preferred embodiments serves in conjunction with the drawings to explain the invention in further detail, in which:

FIG. 8 illustrates deployment of the suture anchor of FIG. 7, in which

FIG. 13A is an exploded view of a preferred suture anchor device of the invention;

FIGS. 21–22 depicts a suture anchor device according to the invention including two anchoring elements.

DETAILED DESCRIPTION OF THE INVENTION

The suture anchor assembly, according to the invention, generally includes an elongated insertion stem and an approximately cylindrical anchoring element having an axial channel for receiving the insertion stem. In its nonexpanded state, the anchoring element can be placed into a pre-drilled opening in a bone. An expander element is engaged with a proximal end of the anchoring element. The term "proximal" refers to a point that is spaced-apart from the bottom of a bone hole in a direction towards the point of origin of the assembly (i.e. towards the surgeon), as opposed to a "distal" point that is closer to the bottom of the bone hole (i.e. farthest from the point of origin; the surgeon). The anchoring element is capable of moving proximally within the bone hole (i.e. towards the bone surface) so that the proximal end of the anchoring element telescopes over a distal end of the expander element. As a result of this movement, resilient proximal portions of the anchoring element are forced outward against the expander element, causing the resilient proximal portions of the anchoring element to expand into the bone hole, fixing the anchoring element in a pressure fit firmly within the opening. The term "telescopes" has its commonly understood meaning in this context and refers to surfaces that slide against each other in which one surface is forced into another. In particular, the distal end of the expander is forced into the proximal end of the moving anchoring element.

A. THE INSERTION STEM

Figure 1:
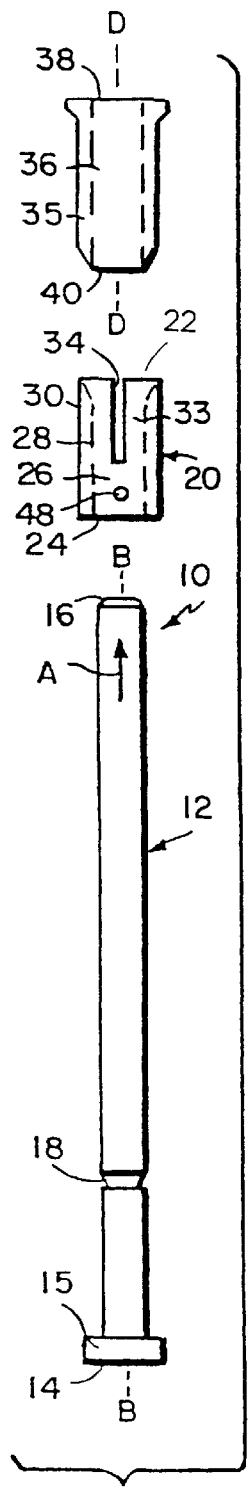
FIG. 1 is an exploded view of a suture anchor of the invention.

FIG. 1 illustrates an exploded view of one embodiment of the suture anchor assembly of the invention containing an insertion stem onto which is loaded an anchoring element and an expander element.

One component of the suture anchor assembly 10 is an insertion stem 12, an elongated cylinder having distal 14 and proximal 16 ends. Distal end 14 is preferably formed as a shoulder 15 designed to engage a distal end 24 of an anchoring element 20. The insertion stem 12 has a frangible portion 18 disposed some distance proximal to end 14. The term "frangible" refers to a portion of stem 12 that is breakable or fragile. In particular, FIG. 1 illustrates frangible portion 18 as a section of stem 12 having a thinner diameter than the remainder of the stem. The frangible section 18 is designed to sever or break when sufficient tension is applied to the stem 12 in a proximal direction (shown by arrow A) that is parallel to longitudinal axis (B—B) of the stem. The frangible portion, however, may be other than a thin-walled section of stem 12 and may include a series of spokes or webbing or a plurality of very attenuated membranes.

B. THE ANCHORING ELEMENT

Anchoring element 20 is substantially tubular, having opposed proximal 22 and distal 24 ends connected by way of a central axial channel 26 extending from the proximal end 22 of element 20 to the distal end 24 of the element. Distal end 24 is engaged with shoulder 15 of stem 12. Element 20 has inner 28 and outer 30 peripheral surfaces forming a wall. Defined in the wall, and in communication with axial channel 26, are a series of axially-oriented slots 34 that begin at the proximal end 22 and extend some distance towards the distal end 24.

Each of the series of axially-oriented slots 34 in the anchoring element 20 define a flexible wall section 33 located between each slot. Each wall section 33 is more flexible at its respective proximal end, in part because the wall section is defined between slots that extend directly from the proximal end 22 of the anchoring element. The distal ends of the respective wall sections 33 are co-extensive with the distal end 24 of anchoring element 20.

FIG. 1 also illustrates a suture retainer 48 located adjacent the distal end 24 of anchoring element 20. Suture retainer 48 is most preferably an aperture for receiving an intermediate portion of a suture (i.e. a segment between the free ends of the suture). This allows the anchoring element to be a so-called "slidable" suture anchor. The suture retainer may be configured in a variety of other ways, including any number of suture retaining configurations, such as a slit, a groove, a clip or wire and the like (e.g., suture engaging slot 221 of stem 212, described above).

C. THE EXPANDER ELEMENT

Expander element 35 is substantially tubular, having opposed proximal 38 and distal 40 ends connected by way of a central axial channel 36, the axial channel defining a longitudinal axis (D—D). The respective inner diameters of the expander element 35 and anchoring element 20 are of sufficient size to allow them to be loaded onto stem 12, anchoring element 20 being engaged first, so that proximal end 22 of the anchoring element 20 is engaged in facing relationship to distal end 40 of expander element 35.

Figure 2:
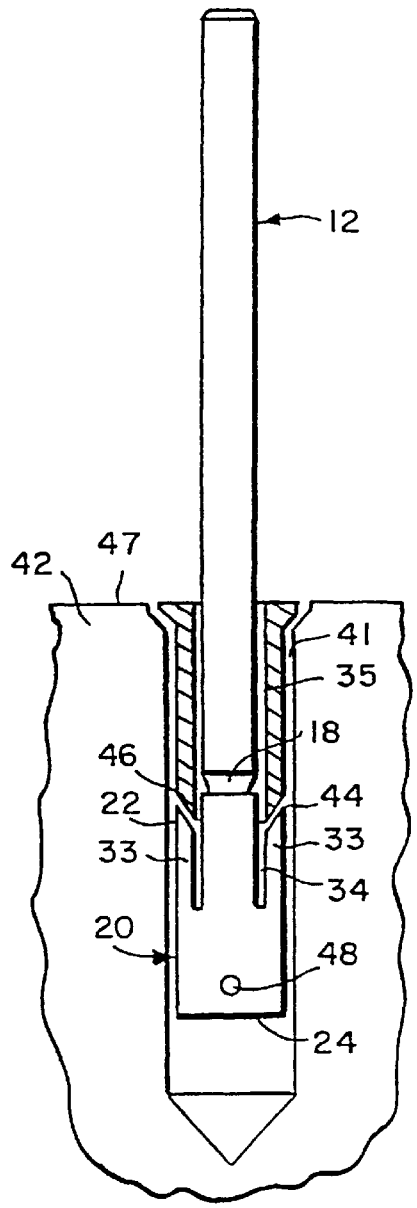
FIG. 2 is a partial cut-away view through the suture anchor of FIG. 1 emplaced in a bone hole.

This is shown in FIG. 2 which illustrates in partial cross-section the configuration resulting when anchoring element 20 and expander element 35 are disposed by way of stem 12 into a hole 41 drilled in a bone 42. The proximal end 22 of each of the flexible wall sections 33 has a camming surface 44 that is designed to mate with a corresponding camming surface 46 at the distal end of the expander element 35. The camming surface 46 of expander element 35 is preferably tapered or beveled, the taper ranging from about 10 degrees to about 45 degrees, relative to axes (B—B) and (D—D). Most preferably, the tapered camming surface is at an angle of about 30° degrees relative to these longitudinal axes. Corresponding tapered camming surfaces 44 of the anchoring element 20 are also disposed at the proximal end 22 of wall sections 33.

Figure 3:
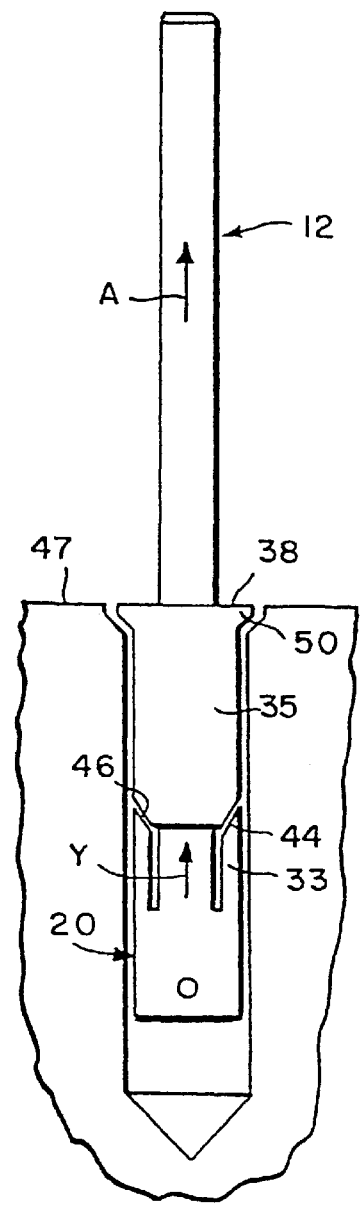
FIG. 3 is a plan view of the embodiment of FIG. 2.
Figure 4:
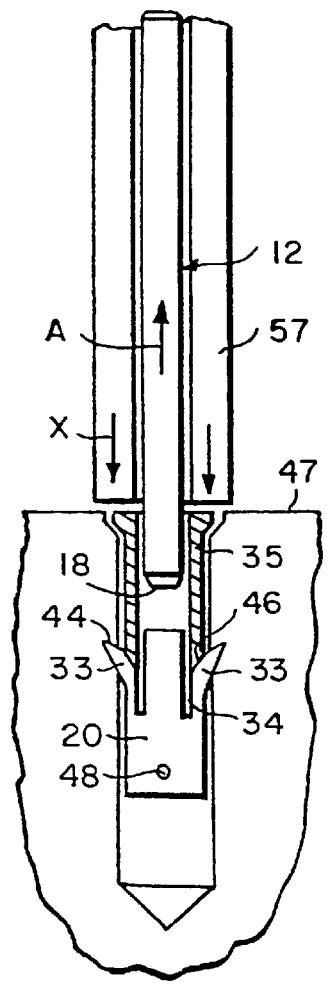
FIG. 4 is a partial cut-away view through the suture anchor of FIG. 1 as it is being deployed in a bone hole.

FIGS. 3 and 4 illustrate operation of this embodiment of the suture assembly and the forces imposed on the components of the assembly in order to set the suture anchor into a bone hole 41. Expander element 35 is substantially fixed at the bone surface 47 and this may be accomplished by using an expander element 35 containing a flange 50 that is integral with the proximal end 38 of element 35 and extending radially outwardly around the periphery of the proximal end 38. In this embodiment, flange 50 serves as a support/countersink to brace the expander element 35 against the bone surface 47 and against a housing 57 of the stem 12 (Shown in FIG. 4) to provide a solid surface onto which a force is exerted that is opposite to the tension force applied to stem 12.

Figure 6:
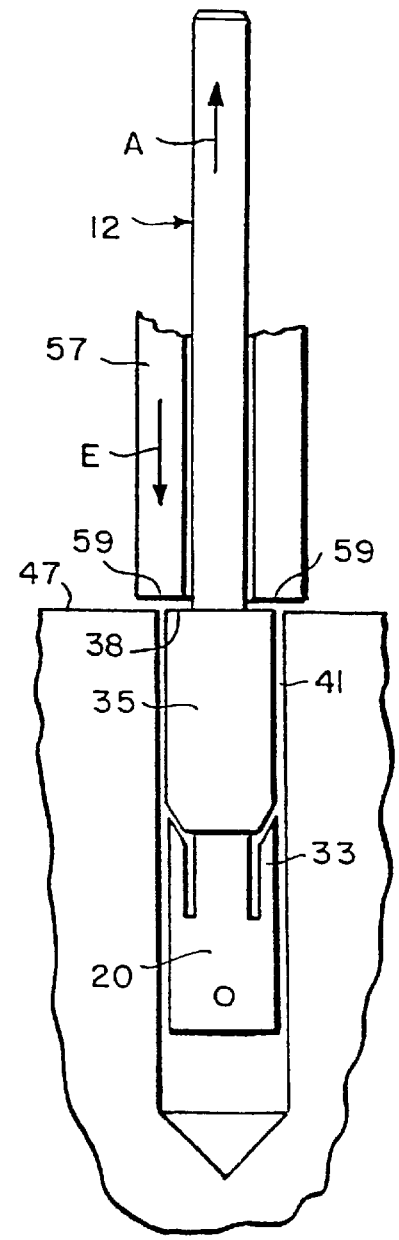
FIG. 6 is a plan view of another embodiment of the suture anchor emplaced in a bone hole.

When tension is applied to stem 12 (in the direction shown by arrow A), the stem 12 and anchoring element 20 are forced in the indicated direction (i.e. proximal to the bone hole) but the expander element 35 remains substantially immobile within the bone hole 41 as the result of a distally-applied counterforce (arrow X) exerted against flange 50 by a distal end 59 of the stem housing 57 (See also FIG. 6). A proximally directed force that is substantially equal in magnitude and in direction to the stem tension force (arrow A) is applied to the proximal end of anchoring element 20. The anchoring element moves proximally in the bone hole and camming surfaces 44, 46 are forced into mating engagement.

As shown in FIG. 4, anchoring element 20 telescopes over the substantially fixed expander element 35. In the embodiment illustrated, distal camming surfaces 46 of expander element 35 remain substantially fixed in position within the bone hole and proximal camming surfaces 44 of anchoring element 20 are forced to ride over them.

Figure 5:
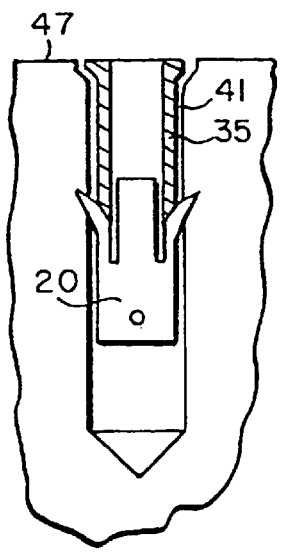
FIG. 5 is a partial cut-away view through the suture anchor of FIG. 4 after emplacement in a bone hole.

Wall sections 33 defined between the series of axially-oriented slots 34 are flexible and will expand into the bone when the camming surfaces are mutually engaged and the anchoring element 20 telescopes over the expander element 35 when tension is applied to the stem 12. Wall sections 33 have proximal ends that are more flexible then other portions thereof. As a result, expansion of the wall sections 33 by the telescoping movement of the anchoring element 20 over the fixed expander element 35 results in the wall sections 33 having a substantially arcuate cross section when fully deployed and expanded in the bone, the proximal ends of the wall sections being driven radially outward and in an oblique direction (i.e., at an angle relative to the longitudinal axis of the stem). The frangible portion 18 of stem 12 is adapted to break when the flexible wall sections are in their fully expanded position. Once severed, the stem 12 may be removed from the rest of the assembly, leaving the anchoring element 20, expander element 35 and attached suture (not illustrated) locked in the bone hole (See FIG. 5). The frangible portion 18 of insertion stem 12 is preferably located at a distance above the distal end 14 of the stem so that, when the stem is removed, the remaining severed stub of the insertion stem does not extend above the level of the bone surface 47.

In other embodiments of the invention, expander element 35 need not have a proximal flange 50. FIG. 6 is a partial, plan section of a bone hole 41 into which a non-flanged expander element 35 is disposed. The distal end 59 of stem housing 57 is wide enough so that it is partially coextensive with the bone hole 41 opening and thus simultaneously contacts both the bone surface 47 and proximal end 38 of expander element 35. Functionally, this configuration may be considered similar to that of FIG. 3 because engagement of proximal end 38 of expander element 35 and the distal end 59 of stem housing 57 also serve to set up a counterforce (arrow E) in opposition to the tension force applied to the insertion stem 12, the counterforce sufficient to fix element 35 in position within bone hole 41.

Figure 7:
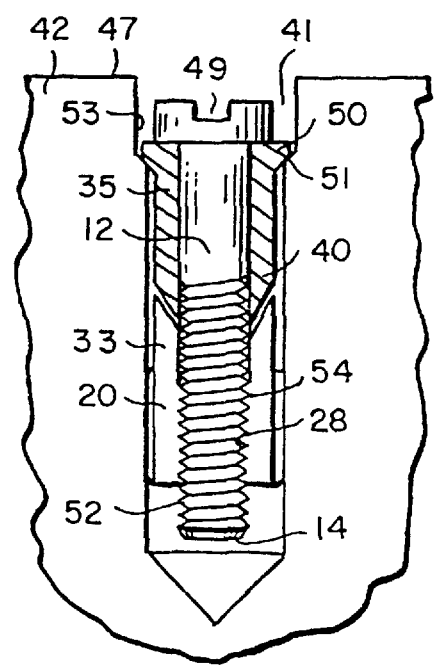
FIG. 7 is a partial cut-away view through a third embodiment of the suture anchor emplaced in a bone hole.
Figure 8A:
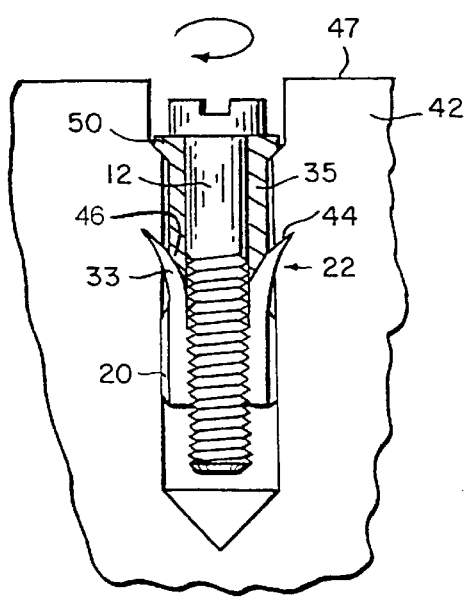
FIG. 8A illustrates deployment of the suture anchor and FIG. 8B illustrates removal of the insertion stem from the bone hole.
Figure 8B:
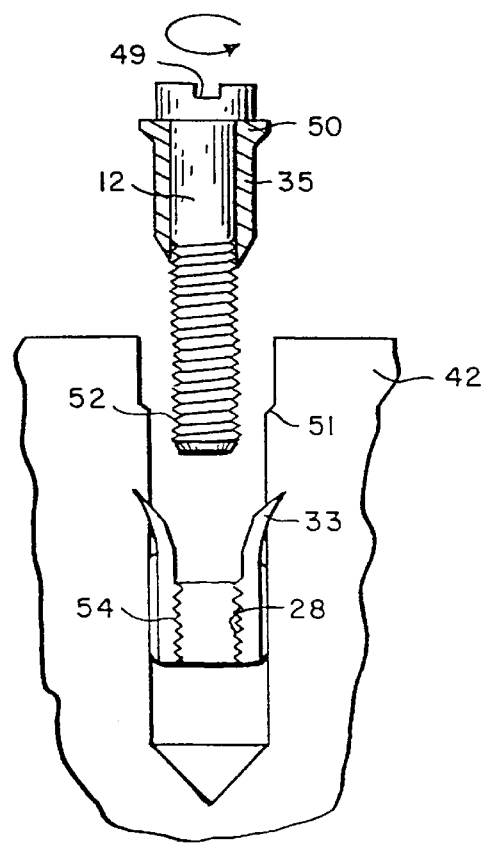

In further embodiments, illustrated in FIG. 7, distal portions of insertion stem 12 may include screw threads 52 for mating engagement with corresponding screw threads 54 on the inner surface 28 of anchoring element 20. Stem 12 includes a proximal slot 49 for engagement with a screwdriver. Expander element 35 may include proximal flange 50 and stem 12 is rotatable within the expander 35. Expander element 35 is countersunk into the bone so that flange 50 rests upon a shoulder 51 defined in the wall 53 of the bone hole 41. The screw threads 52,54 provide for positioning of the anchoring element 20 in the hole 41 at its desired depth and for applying a desired telescoping force to the anchoring element by turning the insertion stem 12 into the axial channel 26 of the anchoring element 20. In such a turnable screw thread configuration, illustrated in FIG. 8A, as the threaded insertion stem 12 is turned clockwise, the expander element 35 remains fixed in the bone hole 41 by way of counterforce pressure against flange 50, but the proximal end 22 of anchoring element 20 is forced to telescope over the distal end 40 of expander element 35 as the threads on the insertion stem are turned. Camming surfaces 44,46 engage and flexible wall sections 33 are expanded into the bone 42. Once the anchoring element is fixed into the bone, the stem and expander may be released by backing out the threaded stem (See FIG. 8B).

In another embodiment of the assembly, the distal end 14 of insertion stem 12 and the distal end 24 of anchoring element 20 are attached as an integral unit so that only the expander element 35 need be loaded onto the insertion stem. Alternately, the assembly may comprise the integral anchoring element and insertion stem and an expander element that is molded to, or extruded integrally with, a distal end of a housing as described below with reference to FIG. 9.

The component parts of the suture anchor assembly may be fabricated by conventional molding or extrusion procedures. Element 20 is preferably constructed of a biocompatible material. The term "biocompatible" means that the anchoring element material is chemically and biologically inert. Suitable materials for the anchoring element include, for example, an implant grade high density polyethylene, low density polyethylene (PE 6010 and PE 2030); acetal (trademark "Delrin", manufactured by Dupont Chemical Co.) and polypropylene (13R9A and 23M2: all made by Rexene, Dallas, Tex.). Of these, PE 6010 and 13R9A have been FDA listed as class 6 materials.

The anchoring element may also be bioabsorbable. The term "bioabsorbable" refers to those materials that are meant to be decomposed or degraded by bodily fluids, such as, for example, blood and lymph. The anchoring element is preferably made from a biodegradable polymer or copolymer of a type selected in accordance with the desired degradation time. That time in turn depends upon the anticipated healing time of the tissue which is the subject of the surgical procedure. Known bioabsorbable polymers and copolymers range in degradation time from about 3 months for polyglycolide to about 48 months for polyglutamic-co-leucine. A common bioabsorbable polymer used in absorbable sutures is poly (L-lactide) which has a degradation time of about 12 to 18 months. The preferred anchoring element is comprised of an absorbable copolymer derived from glycolic and lactic acids, such as a synthetic polyester chemically similar to other commercially available glycolide and lactide copolymers. Glycolide and lactide degrade and absorb in the body by hydrolysis into lactic acid and glycolic acid which are then metabolized by the body.

The following Table set forth below lists polymers which are useful for the bioabsorbable material employed for the anchoring element, and other parts of the bone fastener as described below. These polymers are all biodegradable into water-soluble, non-toxic materials which can be eliminated by the body.

TABLE

| | |
|---|---|
| Polycaprolactone | Poly (L-lactide) |
| Poly (DL-lactide) | Polyglycolide |
| 95:5 Poly (DL-lactide-co-glycolide) | Polydioxanone |
| Polyesteramides | |
| Copolyoxalates | |
| Polycarbonates | |
| Poly (glutamic-co-leucine) | |
| 90:10 Poly (DL-lactide-co-glycolide) | |
| 85:15 Poly (DL-lactide-co-glycolide) | |
| 75:25 Poly (DL-lactide-co-glycolide) | |
| 50:50 Poly (DL-lactide-co-glycolide) | |
| 90:10 Poly (DL-lactide-co-caprolactone) | |
| 75:25 Poly (DL-lactide-co-caprolactone) | |
| 50:50 Poly (DL-lactide-co-caprolactone) | |

D. APPARATUS FOR DEPLOYMENT

A preferred deployment apparatus of the invention retains the insertion stem, expander element and anchoring element prior to emplacement and includes a tool for exerting tension on the insertion stem. The preferred apparatus also allows for separating the insertion stem and expander element from the anchoring element after the frangible section is severed.

Figure 9:
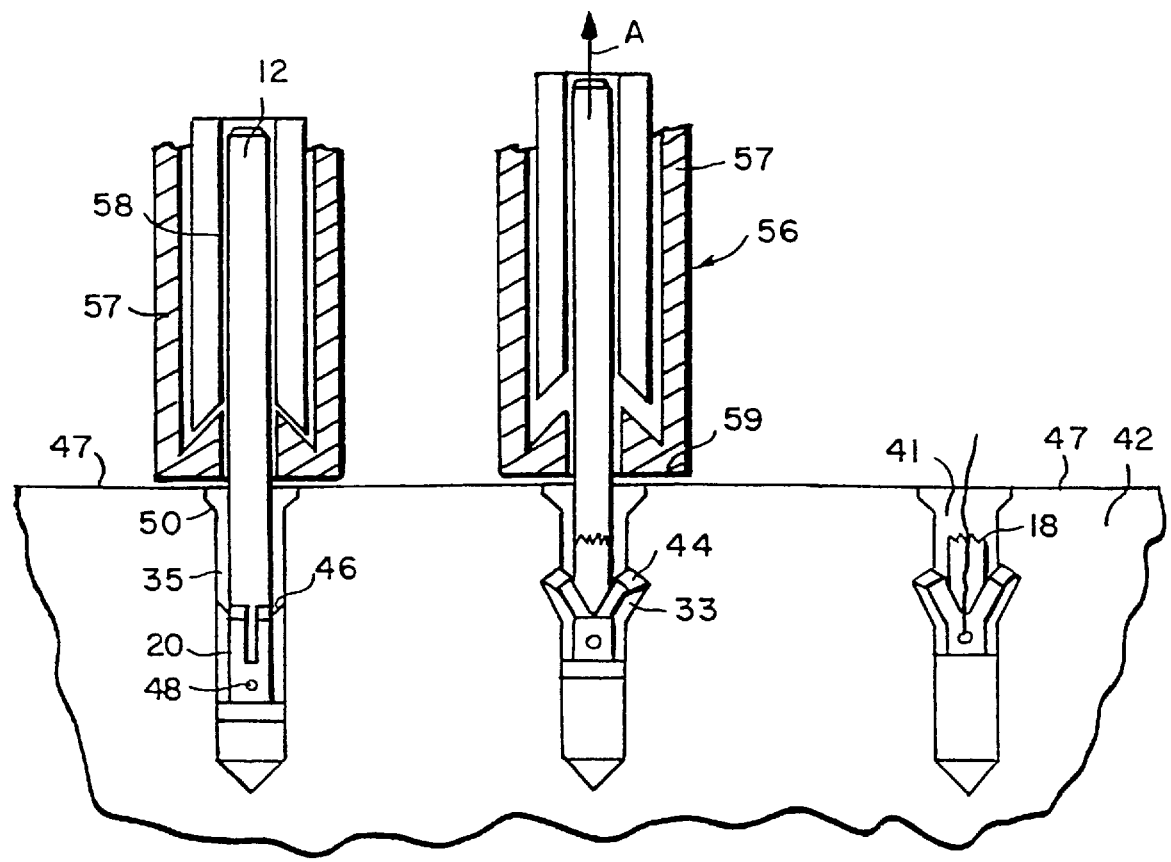
FIG. 9 is a partial, cut-away view of deployment of the suture anchor of FIG. 1 using a pop-rivet gun.

FIG. 9 is a partial, plan view illustrating one embodiment of a deployment apparatus of the invention and its mode of operation. The insertion stem 12 is pre-loaded with the anchoring element 20 and the expander element 35 and the stem 12 is then placed into an apparatus similar to a pop-rivet gun 56. The stem 12 is encased within a housing 57 of the apparatus so that a toothed collet 58 or other similar grasping means engages the insertion stem 12. The anchor assembly is then placed in a hole 41 drilled into a bone 42 and a distal end 59 of the housing 57 is pressed into contact with the bone surface 47. This helps fix the flange 50 of expander element 35 into position at the bone surface 47. Activation of the apparatus 56 retracts the insertion stem 12 proximally (arrow A) to induce tension on the stem. The camming surfaces 44,46 of the respective anchor 20 and expander 35 elements come into telescoping contact and the flexible wall sections 33 of anchoring element 35 are set into the bone 42. Tension is continually exerted on stem 12 until the stem shears off from the remainder of the suture assembly at the frangible section 18. In those embodiments of the apparatus in which expander element 35 is molded or extruded integrally as one-piece with distal end 59 of housing 57, once the stem is sheared the rest of the stem and the expander element are removed to leave the anchoring element with its attached suture (and severed stem) in the bone. In the other embodiments where the expander element is not integral with the housing, the severed stem and the expander element are left in the bone.

Figure 10:
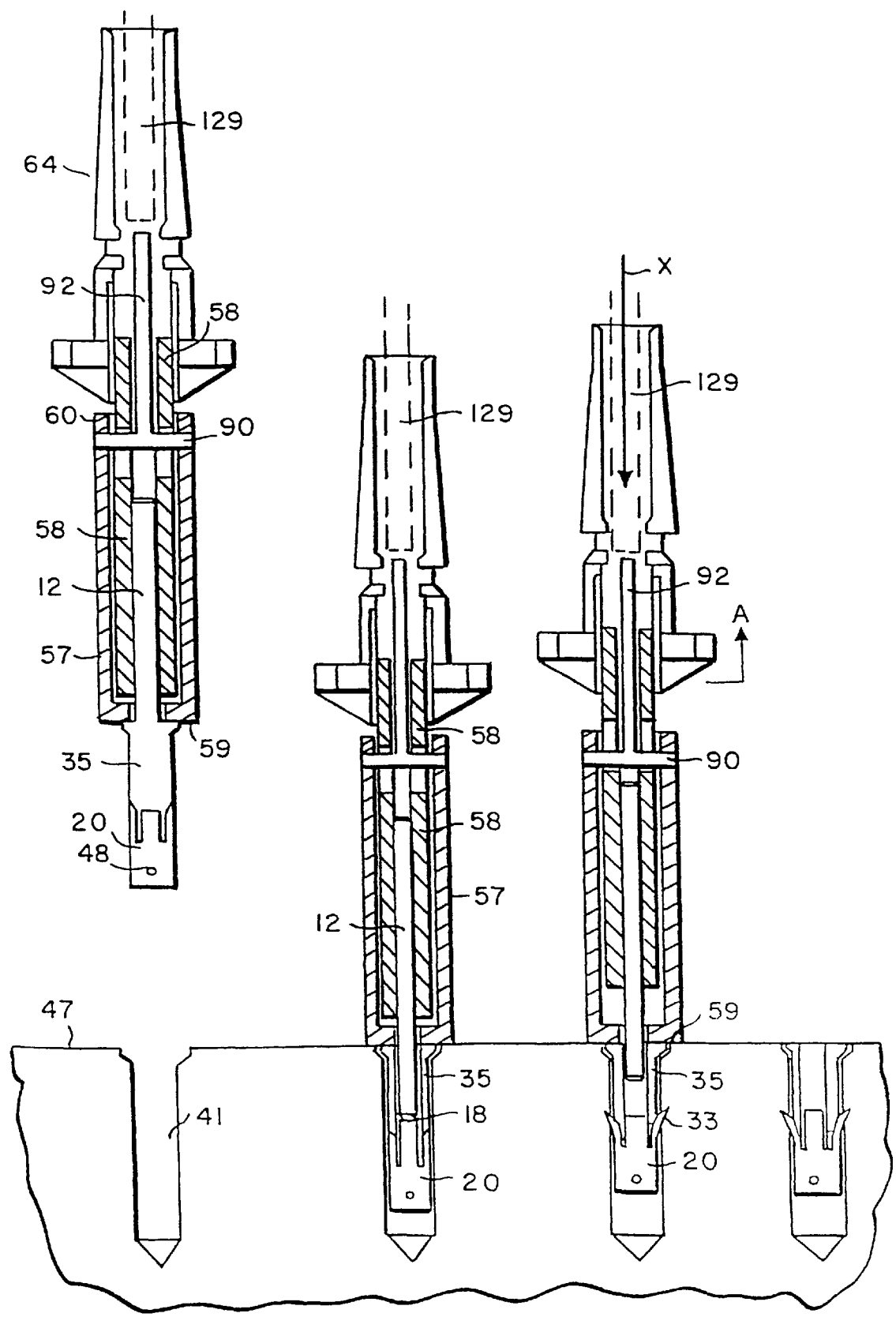
FIG. 10 is cut-away view of another embodiment of the suture anchor deployment device.

FIG. 10 illustrates another embodiment of an emplacement apparatus of the invention and its mode of operation. The apparatus includes a housing 57 which encloses insertion stem 12 held co-axially in place by a toothed collet 58. The proximal end 60 of the housing 57 is engaged with arms 90 of a push rod 92 in the shape of an inverse T. Proximal end 60 of housing 57 also includes an aperture (not shown) for receiving the collet 58. The collet 58 is integral with a bayonet-type connector 64 that allows the combined connector and housing to be removably attached to a hand held means 120 (See FIG. 11). The stem 12 is thus co-axially arranged around the collet 58 and the collet can move co-axially within the housing 57. The anchoring element 20 and expander element 35 are threaded on the stem and the stem 12 is positioned in the collet.

Figure 11:
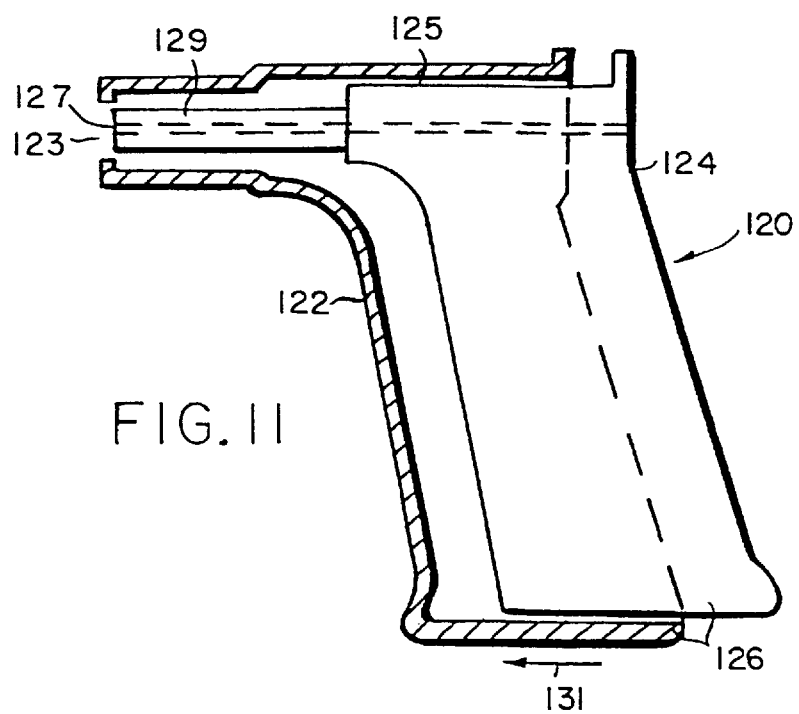
FIG. 11 is a cross-sectional view of a hand-held deployment means used with the device of FIG. 10.

Referring now to FIG. 11, the hand-held means 120 is of similar design to the hand held means described in co-pending and commonly assigned patent application Ser. No. 08/163,130, "Bone Fastener", filed Dec. 6, 1993, incorporated herein by reference. Briefly, the hand held means 120 consists of two handle elements 122, 124 slidably engaged to provide a comfortable pistol grip 126 by which handle element 124 can be moved in a proximal-distal direction with respect to the handle element 122 by squeezing the pistol grip 126. The distal end 123 of the handle element 122 is adapted for removably mounting the bayonet connector 64. The distal end 125 of handle element 124 includes a rod 129 whose distal end 127 abuts push rod 92 when the handle elements are assembled and the connector 64 is mounted onto end 123 of handle element 122.

With the apparatus so assembled, the surgeon grasps the apparatus by the pistol grip 126, and directs the anchoring assembly into the predrilled hole in the bone. The distal end 59 of the housing 57, and optionally the flange 50 of the expander element, engage the bone surface. Then, the surgeon squeezes the grip 126 sliding the handle 124 frontward with respect to the handle element 122, as indicated by the arrow 131. Rod 129 presses against push rod 92 in the distal direction (arrow X in FIG. 10) and the downward force is transmitted through the inverse-T arms 90 to the housing 57 and against the bone surface 47. At the same time, the connector 64 and attached co-axially moveable stem 12 are urged proximally (arrow A), translating the distal force on the push rod 92 to a proximal, tensioning force on the insertion stem 12.

E. APPARATUS FOR REMOVAL

Figure 12:
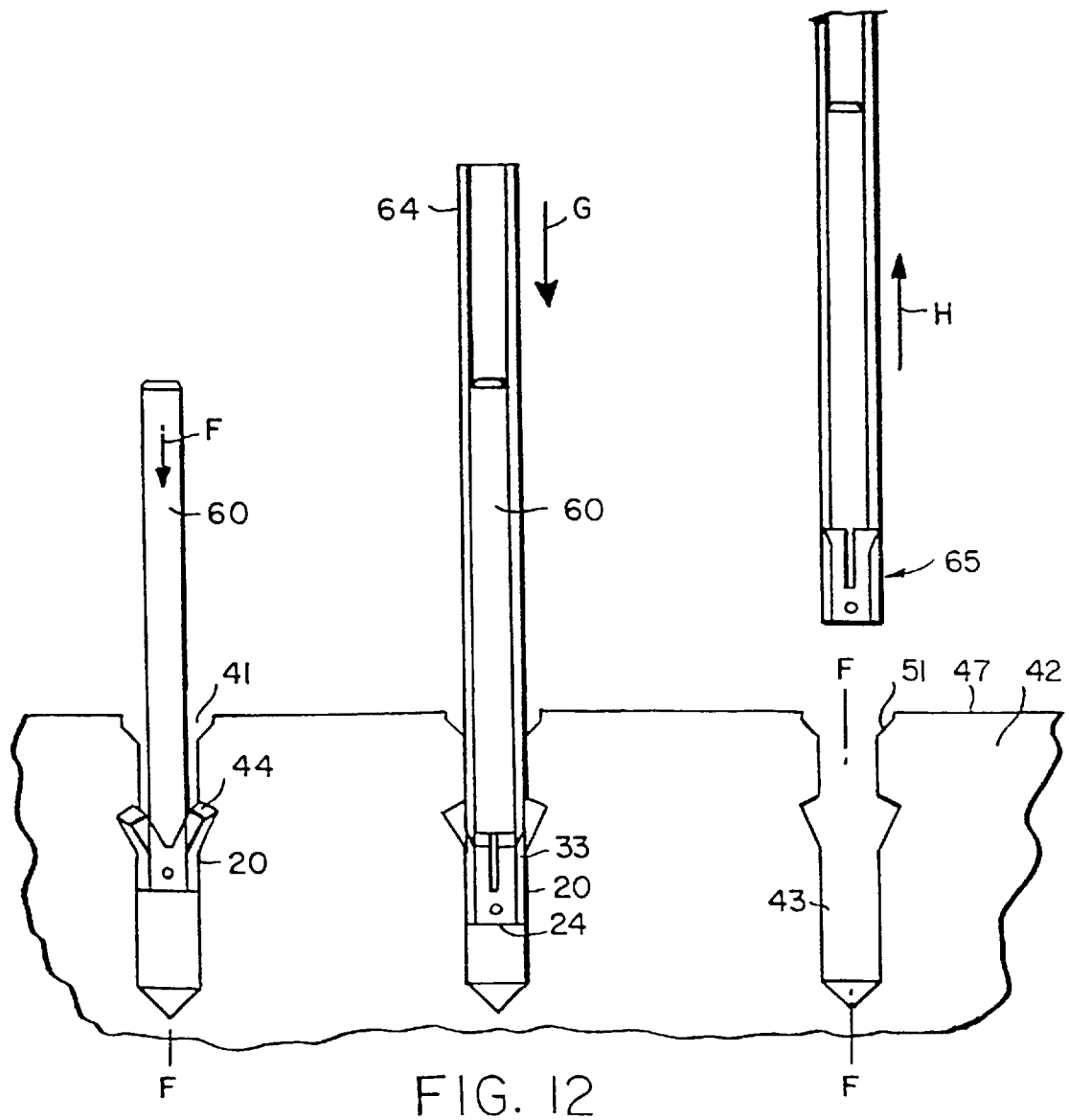
FIG. 12 is a cut-away view of a device and method for removing the suture anchor of the present invention.

A significant feature of the present suture assembly is that the anchor element may be removed after deployment by forcing the anchoring element distally back down into the bone hole 41. A removal apparatus as illustrated in FIG. 12 consists of a cannulated rod 60 whose distal end 62 is adapted to engage with distal end 24 of anchoring element 20 or with the severed end of the insertion stem 12 at the frangible section. As illustrated, rod 60 is engaged with anchoring element 20 and pressed distally (arrow F) to drive the anchor element 20 back down into the bone hole until the flexible wall sections 33 are substantially parallel to the longitudinal axis (F—F) of the bone hole and extend in a proximal -distal direction. A sheath 64 is then slid (arrow G) over the rod 60 to engage outer peripheral surfaces of the anchoring element 20. This engagement may be facilitated by a series of detents (not shown) located on the distal end 65 of sheath 64 which fixedly engages the anchoring element. The anchoring element, any insertion stem remaining, and sheath are removed (arrow H) from the bone hole as a unit.

F. METHODS

One method, although by no means the only method, for attaching soft tissue to bone will be described below.

To attach soft tissue to bone, a surgeon takes the sharpened proximal end of a K-wire (manufactured, for example, by Kirschner Medical Company) and spears the tissue that is to be attached. The proximal end of the K-wire is then placed over the bone surface at the approximate site of attachment. The K-wire is then drilled into the bone at that site. If the location is where the surgeon wants it, the surgeon then threads a cannulated drill of the appropriate size over the K-wire. A hole is then drilled into the bone using the cannulated drill. Then drill and K-wire is are removed. It will be understood that the use of a K-wire is not essential to this method of drilling a bone hole.

Whether or not the K-wire is used, the suture assembly of the invention is then loaded within an emplacement apparatus (for example, described above with reference to FIGS. 9–11). The assembly is pressed downwards through the tissue and into the bone hole so that the anchoring element is emplaced into the bone hole. If the surgeon decides that the orientation of the assembly and soft tissue is correct, the emplacement apparatus is triggered by applying a tensional force to the insertion stem so that the proximal end of the anchoring element telescopes over the distal end of the expander element. The outer, flexible surfaces of the anchoring element engage with the bone and the insertion stem is released from the anchoring element to set the anchor element within the bone hole. The apparatus is removed. Other variations on this technique include first drilling a bone hole and then punching a hole through the soft tissue. The tissue is then moved over the bone hole using, for example, a K-wire or a suture passer grasping device.

It is an important feature of the present invention that the force needed to telescope the anchoring element may be substantially continuous and spread out over time. The anchoring element is telescoped over the expander element with a compressive motion that is axially delivered in a direction substantially parallel to the longitudinal axis of the insertion stem. Thus, the apparatus for deploying the present assembly requires an advancing drive mechanism which lacks any impact or impulse characteristics.

The components of the bone fastener of the invention may be included in a surgical fastener kit. An exemplary kit may include an anchoring element of the invention; an insertion stem of the invention and a holder for engaging with the anchoring element, the holder capable of maintaining the anchoring element in position with the bone opening. Other embodiments of the kit may include a grasper/manipulator for grasping free ends of the suture to pass the suture through soft tissue. Such a suture-grasping device is described in commonly assigned and co-pending application Ser. No. 08/097,154, filed 26 Jul. 1993, incorporated herein by reference. A K-wire, drill and drill guide may also be also included. Preferably, the kit is encased in a sterile tray or other receptacle for use by an operator at a site.

The invention will now be illustrated by the following non-limiting examples.

Three different polysulfone anchor elements were fabricated by machining polysulfone, extruded bar stock. The elements included several of 2.8 mm length (wall thickness of 0.018, 0.024 and 0.035 inches); 3.5 mm long (0.018" wall thickness) and 3.8 mm long (0.025" wall thickness). Anchors were attached to sutures and were set using the procedures described herein into an artificial bone made of foam made by Sawbones, Inc., P.O. Box 589, Vashon, Wash. 98070. Tension was applied to the sutures by a stainless steel hardened wire attached to the back of the anchor. Tension was measured by a force gauge. The foam/suture assembly was observed for anchor failure. Results are presented below in the Table.

| Diameter (mm) | Wall (inches) | Force (lb) | Observations |
|---|---|---|---|
| 2.8 | 0.018 | 29.0 | Failure; 3 wall sections bent back on themselves; foam cone pulled out 0.25" diameter |

-continued

| Diameter (mm) | Wall (inches) | Force (lb) | Observations |
|---|---|---|---|
| | 0.024 | 32.8 | Failure; 4 wall sections bent back on themselves; foam cone pulled out 0.23" diameter |
| | 0.035 | 33.4 | Failure; 4 wall sections bent back on themselves; foam cone pulled out 0.23" diameter |
| 3.5 | 0.018 | 37.2 | Failure; anchor broken with half pulled through; wall sections on the broken half were straight. |
| | 0.018 | 43.0 | Failure; wall sections bent back over themselves |
| 3.8 | 0.025 | 33.0 | No anchor failure; foam bone wedge pulled out and only 2 wall sections were spread; foam pullout .5" diameter/.25" deep |
| | 0.025 | 51.0 | No anchor failure; all wall sections spread; foam bone wedge pulled out; .75: diameter/.25" deep |

G. FURTHER EMBODIMENTS

FIG. 13A depicts an insertion stem 212 according to a preferred practice of the invention. As with the stem 12 depicted in FIG. 1 and described in connection therewith, the stem 212 is elongate and has distal 214 and proximal 216 ends. Distal end 214 is formed with a shoulder (or head) 215 designed to engage a distal end 224 of an anchoring element 220. The insertion stem 212 has a frangible portion 218, disposed some distance proximal from end 214, and designed to sever or break when sufficient tension is applied to the stem 212 in a proximal direction parallel to longitudinal axis of the stem. As above, the frangible portion may be other than a thin-walled section of stem 12 and may include a series of spokes or webbing or a plurality of very attenuated membranes.

The stem 212 includes threading 217 for threaded engagement by the deployment apparatus of FIGS. 9–11. Ridges 219, which are disposed distal of frangible portion 218 of stem 212, provide ratchet-like retention of the expander element 235 in the assembled suture anchor assembly, thereby preventing unwanted or excess movement of the expander element relative to the anchoring and insertion elements. Suture engaging slot 221 provides a track in which a loop of a suture may be retained, thereby providing additional control over the suture, e.g., for purposes of knot-tying.

With continued reference to FIG. 13A, like anchoring element 20 depicted in FIG. 1 and described in connection therewith, anchoring element 220 is substantially tubular, having opposed proximal 222 and distal 224 ends connected by way of a central axial channel (not shown) extending from the proximal end 222 to the distal end 224. Distal end 224 engages with shoulder 215 of stem 212. As above, element 220 has inner and outer peripheral surfaces forming a wall. Defined in the wall, and in communication with the axial channel, are a series of axially-oriented slots 234 that begin at the proximal end 222 and extend some distance towards the distal end 224. Each of the series of axially-oriented slots 234 in the anchoring element 220 define a flexible wall section 233 located between each slot. The anchoring element can include a plurality of slots 234 and, thereby, a corresponding number of wall sections 233. Although the number of slots (and wall sections) can range from 2 to 10 (or upwards), a preferred number of slots (and wall sections) is three or four.

Figure 14:
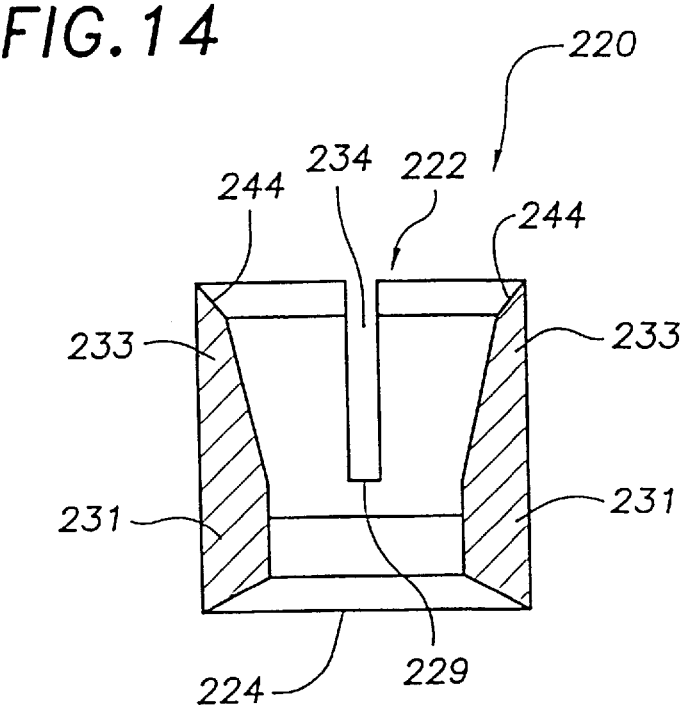
FIG. 14 depicts in cross-section a preferred anchoring element of the suture anchoring device of FIG. 13A.

Referring to FIG. 14, the anchoring element 220 is shown in cross-section. As evident in the drawing, each wall section 233 tapers gradually from a base portion 231 to the proximal end 222. That taper can be, for example, 0° to 20° degrees and, preferably, is about 8°. Camming surfaces 244 at the tips of the walls have more pronounced tapers. These can range, e.g., from 30° to 75° and is, preferably, about 60°.

Figure 13B:
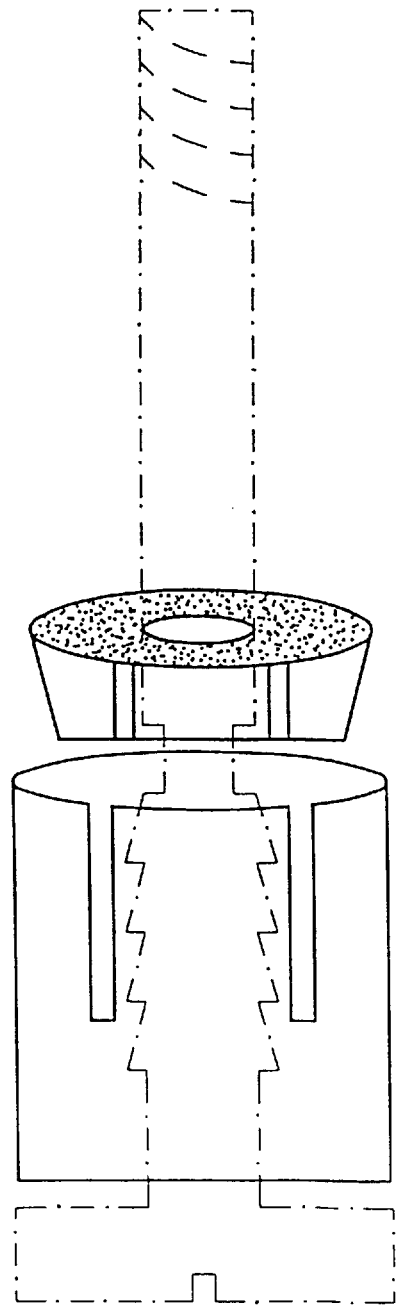
FIG. 13B depicts the suture anchor of FIG. 13A partially assembled.

Referring to FIG. 13A, a preferred expander element 235, like element 35 depicted in FIG. 1 and described in connection therewith, has opposed proximal 238 and distal 240 ends connected by way of a central axial channel 236. The diameter of channel 236 is of sufficient size to allow it to be loaded onto stem 212, along with anchoring element 220, so that proximal end 222 of the anchoring element 220 is engaged in facing relationship to distal end 240 of expander element 235. This is shown in FIG. 13B, which illustrates in partial cross-section the configuration resulting when anchoring element 220 and expander element 235 are are readied for assembly on stem 212.

Referring FIG. 14, the proximal end 222 of each of the flexible wall sections 233 of anchoring element 220 has a camming surface 244 that is designed to mate with a corresponding camming surface 246 at the distal end of the expander element 235. The camming surface 246 of expander element 235 is tapered at approximately 45°, though that taper can be as little as about 10° and as much as 60°.

To prevent the anchoring element 220 from telescoping, or "camming," too far over the expander element 235, the expander element 235 includes projections or wings 237, each of which corresponds with a slot 234 of anchoring element 220. The wings 237 slidingly engage with slots 234 as the suture anchor system is being assembled. This permits the anchoring element 220 to telescope or cam over expander element 235 until the wings 237 reach the bottoms 229 of their respective slots 234. As a less preferred alternative, the anchoring element 220 can include an internal shoulder, or other such protrusion, that prevents the anchoring element 220 from telescoping or camming too far over expander element 235.

Figure 15:
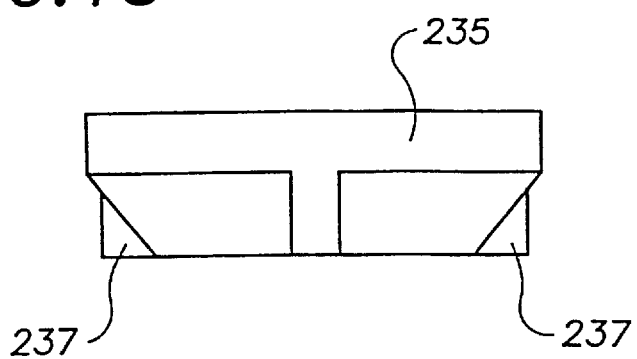
FIG. 15 depicts in side view a preferred expander element of the suture anchoring device of FIG. 13A.

The expander element 235 is shown in side view at FIG. 15. There, it is seen that the element 235 has a height (i.e., length along the longitudinal axis) less than that of the sides 233 of the anchoring element 220. Preferably, the height of element 235 is approximately one-half that of the sides 233 and, still more preferably, a height substantially equal to that of the camming surface 244.

Further embodiments of the invention incorporate refinements that facilitate fabrication of a smaller suture anchoring assembly of the type used in facial reconstructive surgery and other surgeries involving thinner bone structures. These refinements strengthen the assembly by reducing the stresses placed on its components of the assembly and, thereby, prevent failure of the anchoring assemblies during and subsequent to emplacement in the bone structures.

Figure 16:
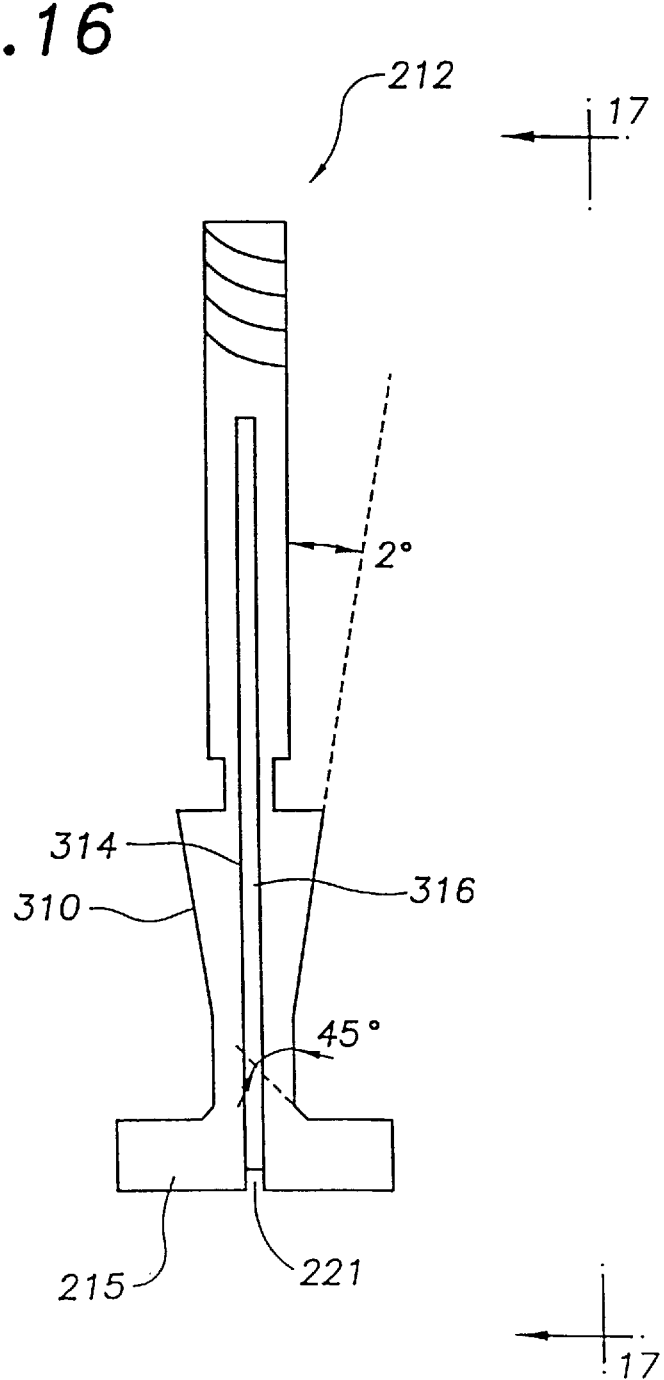
FIGS. 16 and 17 depict an insertion stem incorporated in a preferred suture anchor assembly according to the invention.

At the outset, referring to FIG. 16, the insertion stem 212 incorporates a suture retaining slot 221 that provides a track in which the suture (not shown) is slidingly engaged as it loops over the head 215 of the insertion stem. This slot prevents the suture from sliding off the head 215 during suture knot-tying or during and subsequent to emplacement of the anchor assembly in the bone. In embodiments where the head 215 is integral with the anchoring element, the suture retaining slot may be said to reside at the distal end of the anchoring element 220.

It will be appreciated that looping a suture over the head 215 provides added strength to the overall assembly.

Particularly, when the suture is under tension (e.g., during and subsequent to tying), the suture retaining slot is in compression, as are head 215 and adjacent portions of the stem 212. This configuration gives the suture retainer (and, therefore, the assembly as a whole) greater strength then found in configurations (such as where a suture-retaining aperture is disposed at the proximal end of the insertion stem 212) in which the suture retainer is placed under tension when the suture itself is under tension. Alternatives to the illustrated slot include placing an aperture (e.g., hole) through which the suture can be tied, or a shoulder around which the suture can be looped, at locations on anchoring element 220 or insertion stem head 215 that are distal to the slot ends 229 of the assembled suture anchor device.

With further reference to FIG. 16, a track 314 extends from the slot 221 toward the proximal end of the stem 212. This serves to guide and protect the suture from being crimped by the anchor assembly during and subsequent to its emplacement in bone. The slot and track widths are sized in accord with the expected suture gauge. Preferably, the width is such that the suture can slide freely without excessive width-wise play. The slot and track depths are likewise determined by the expected suture gauge.

Figure 17:
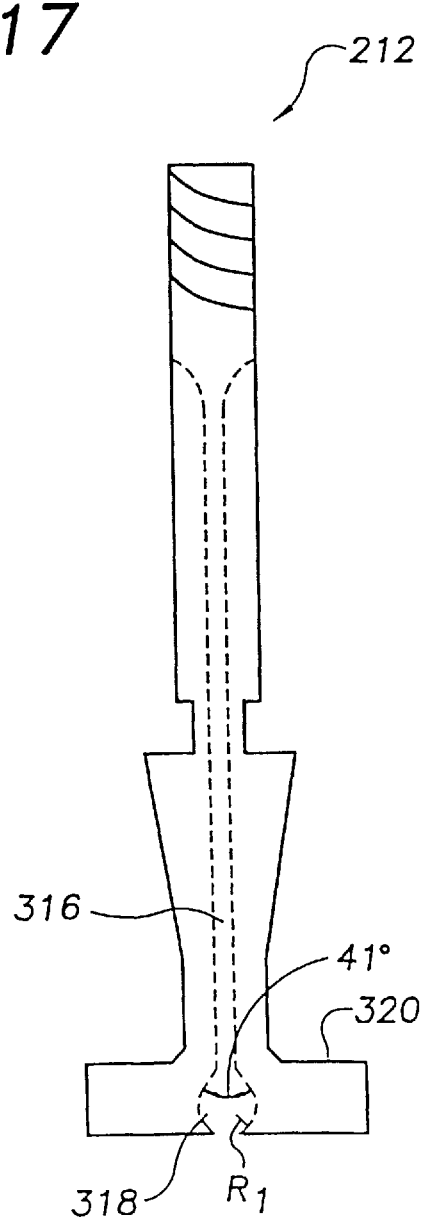

FIG. 17 depicts a side cut-away view of insertion stem 212 and shows the shape of the support base (or floor) 316, at the base of the slot 221 and track 314, supporting the suture. As illustrated, the support base 316 runs longitudinally, parallel to the major axis of the stem 212 and ends in a tear drop shape 318 at the distal end of the stem, i.e., at slot 221, where the suture loops over head 215.

The tear drop shape is advantageous over a conventional rectilinear shape insofar as the tear drop distributes over a greater surface area the compressional load applied to the head 215 by the suture, e.g., during and subsequent to its being tied. As shown in the drawing, the tear drop opens at an angle of 30°–60° and, more preferably, of 41° beginning a point distal to the proximal side 320 of the head. As further illustrated the "corners" of the tear drop 318 define a radius $R_1$ of 0.001–0.020 inches and, preferably, 0.010 inches for a #2 suture. Proportionally sized radii can be selected for where the expected suture gauge differs from this.

Referring back to FIG. 16, the stem 212 incorporates a chamfer at the junction of the elongate portion of the stem and head 215. The chamfer 312, which is angled at 20°–70° and, more preferably, 45°, also serves to reduce the concentration of tensional stress on head 215 during and subsequent to emplacement of the anchor assembly in bone.

A used herein, the term "chamfer" refers to conventional straight-edge chamfers, as well as blend radii.

In a preferred embodiment, the stem 212 incorporates a reverse taper 310 in place of ridges 219 discussed above. The taper 310, which is exaggerated in the drawing for visualization purposes, describes an included angle of 1°–10° and, preferably, of 2°, relative to the longitudinal axis of the stem 212. As above, the reverse taper serves to prevent unwanted or excess movement of the expander element relative to the anchoring and insertion elements.

Figure 18:
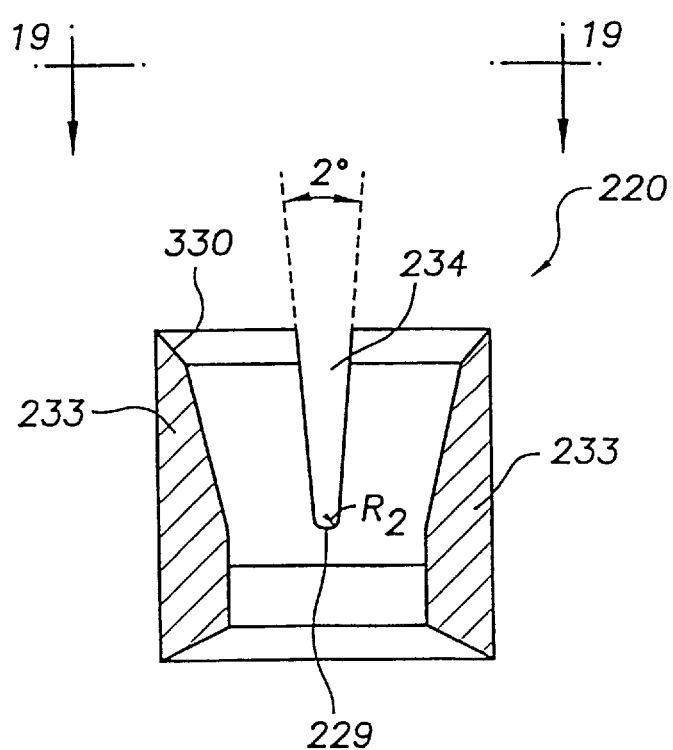
FIGS. 18 and 19 depict an anchoring element incorporated in a preferred suture anchor assembly according to the invention.
Figure 19:
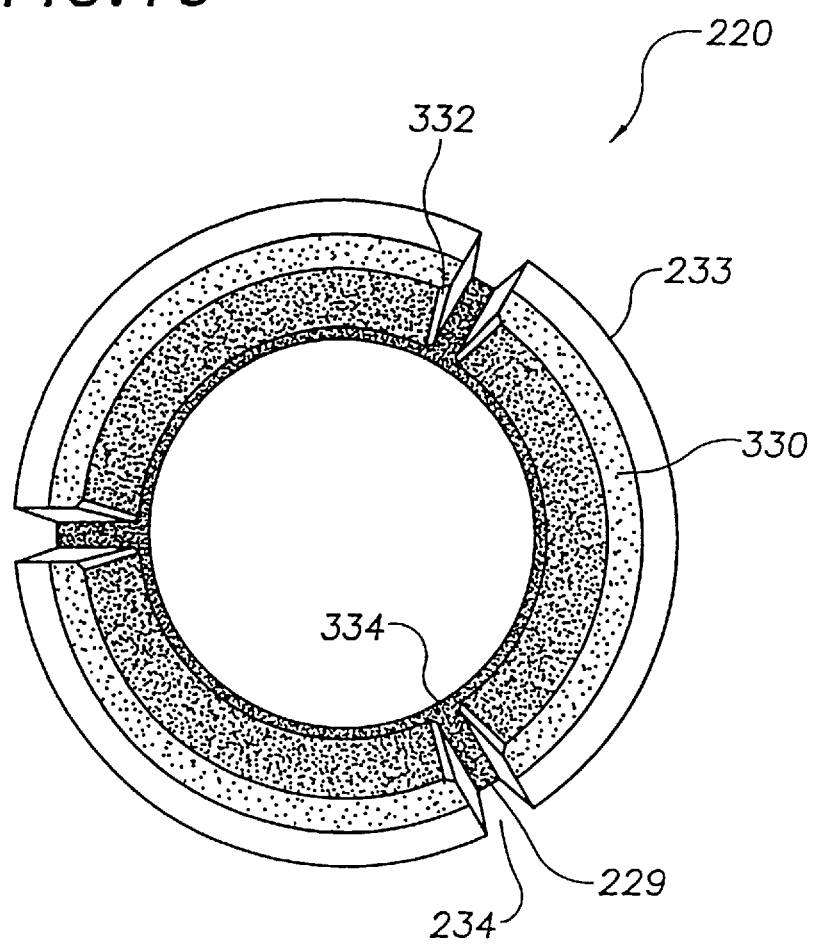

In order to withstand the stresses placed on the walls 233 and slot bases 229 of the suture anchoring assembly and, especially, smaller suture anchoring assemblies, the anchoring element incorporates a number of features to distribute the stresses of emplacement. This gives smaller assemblies, which may be constructed from polymers and copolymers (as described above), greater holding strength without risk of failure. As shown in FIGS. 18 and 19, stress distribution is accomplished by rounding, or chamfering, stress-bearing edges of the walls 233 and slots bases 229, as well as by tapering the walls, in order to distribute applied loads.

For example, as shown in FIG. 18, the distal ends 229 of the slots of anchoring element 220 are rounded. This reduces stress on, and thereby prevents failure of, the anchoring element 220 in the region adjacent to those rounded distal ends. As illustrated, the rounded ends of the slots 234 define radii $R_2$ of 0.001–0.020 in and, preferably, 0.010 in for a three-wing or four-wing polymer anchor having an outside diameter of 3.5 mm, an inside diamter of 2 mm, an overall length of 5.5 mm, and a wing length of 3 mm. Proportionally sized radii can be selected for anchoring elements whose dimensions differ from this.

As further shown in FIG. 18, the slots 234 are tapered. Particularly, they are wider at the proximal end then at the distal end. The degree of taper may vary from 0°–10° and, preferably, is about 2°. This taper also reduces the stress on, and thereby prevents failure of, the anchoring element 220 in the region adjacent to the distal ends of the slots 234.

FIG. 19 is a top view of a preferred anchoring element 220 according to the invention. As shown in the drawing, the edges of wall sections 233 are chamfered to reduce stress during and subsequent to emplacement of the assembly in bone. More particularly, each wall section 233 is chamfered along its inner-top edge 330, as well as along the edges of the slot 234 that defines its inner-side edges 332, as shown. Chamfering along the inner-top edge 330 is preferably accomplished via a blend radius.

For a like-sized anchoring element, the inner-side edges 332 are also chamfered by a blend radius of, e.g., of 0.001–0.020 inches and, preferably, 0.010 inches for a three-wing or four-wing anchor having dimensions as specified above. Again, proportionally sized radii can be selected for anchoring elements whose dimensions differ from this. This chamfering continues along the entire inside edge of each slot 234, including the inside edge 334 at the bottom 229 of each slot.

Figure 20:
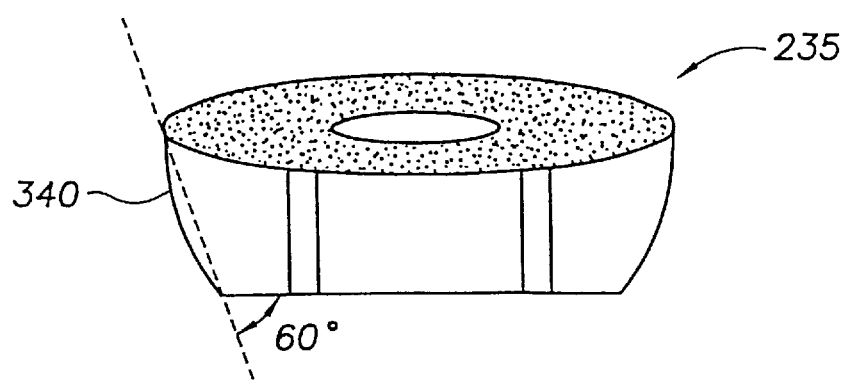
FIG. 20 depicts an expander element incorporated in a preferred suture anchor assembly according to the invention.

Referring to FIG. 20, a preferred expander element 235, can have camming surfaces 340 that are rounded in order to mate with the chamfered inner-top edge 330 of expander element 220. As above, the surface 340 can have an overall angle tapered at approximately 45° (or little as about 10° and as much as 60°). It is rounded to a degree sufficient to allow the wings of the anchoring element to cam over the expander element when opposing force is applied to the anchoring element.

FIG. 21 depicts a suture anchor assembly according to a further embodiment of the invention incorporating two anchoring elements for added strength. The assembly includes, stem 212, anchoring element 220 and expander element 235, as well as additional anchoring element 350. As shown in the drawing, the additional anchoring element 350 is disposed between expander element 235 and the anchoring element 220. Element 350 is constructed in the same manner as element 220 except insofar as its distal end 352 has chamfered camming surfaces 354 similar to surfaces 340 of expander element 235. As above, those camming surfaces 354 can be straight chamfers or blended radii. In either event the surfaces are angled and/or rounded to a sufficient degree allow the wings of the anchoring element 220 to cam over the distal end 352 of element 350 upon assembly of the device, as shown in FIG. 22.

With reference to FIG. 21, it will be appreciated that a suture anchor assembly according to the invention, more generally, may include a plurality of tubular anchoring elements 220, 350, loaded "in series" on the stem 212 as shown. A distal-most anchoring element 220 has its distal end in engagement with the proximal side 320 of the stem's head, while the other anchoring elements 350 having their distal ends in engagement with a proximal end of the adjacent anchoring element.

Upon assembly, the proximal-most anchoring element 350 moves proximally within the bone hole (not shown) from a first position, where that anchoring element's proximal end is engaged with the distal end of the expander element 235, to a second position, where the proximal end cams over the distal end so that flexible wall sections expand, as shown in FIG. 22, into a wall of the bone hole. Likewise, upon assembly, the other anchoring element 220 is adapted for proximal movement within the bone hole from its respective first position, where its proximal end is engaged with the distal end of the adjacent anchoring element 350, to a respective second position, where that proximal end cams over that distal ends, as shown in FIG. 22, so that the respective flexible wall sections expand into a wall of the bone hole.

Although FIGS. 21 and 22 show only two anchoring element, those skilled in the art will appreciate that still further embodiments of the invention may include three or more anchoring elements.

A further appreciation of an exemplary apparatus of the type shown in FIGS. 13A–20 may be attained by reference to the three-dimensional drawings shown in the Appendix filed herewith.

EQUIVALENTS

It should be understood that various changes and modifications of the preferred embodiments may be made within the scope of the invention. Thus, for example, it will be appreciated that, while the illustrated embodiments are constructed of polymers, copolymers, and bioabsorable materials, they can also be contstructed of metals and other biocompatible materials. Thus it is intended that all matter contained in the above description be interpreted in an illustrative and not limited sense. In view of the forgoing,

What we claim is:

1. A suture anchor assembly, comprising:
   a tubular anchoring element having defined therein an axial channel for loading onto a stem and having a distal end for engagement with a distal end of the stem, the anchoring element including inner and outer peripheral surfaces forming a wall therebetween, the wall having defined therein a plurality of axially-oriented slots in communication with the axial channel, the slots beginning at a proximal end of the element and extending distally, wherein the plurality of slots further define a plurality of flexible wall sections disposed between adjacent, axially-oriented slots;
   a tubular expander element having defined therein an axial channel, the expander element for loading onto the stem and having a distal end for engagement with the proximal end of the tubular anchoring element, wherein the tubular anchoring element is adapted for proximal movement within a bone hole from a first position, where a proximal end thereof is engaged with the distal end of the expander element, to a second position, where the proximal end of the tubular anchoring element cams over the distal end of the expander element so that flexible wall sections expand into a wall of the bone hole; and
   a suture retainer coupled to the anchoring element and disposed such that an under-tension suture therein places the suture retainer in compression.

2. A suture anchor assembly according to any of claim 1, wherein the suture retainer is disposed at the distal end of the anchoring element.

3. A suture anchor assembly according to claim 2, wherein the suture retainer comprises a slot disposed at the distal end of the anchoring element.

4. A suture anchor assembly according to claim 3, wherein the suture retainer has a base that is rounded at the distal end of the anchoring element.

5. A suture anchor assembly according to claim 4, wherein the suture retainer has a base that is tear drop shaped.

6. A suture anchor assembly according to any of claim 1, wherein the suture retainer is disposed distal to a distal end of the axially-oriented slots defined in the walls.

7. A suture anchor assembly according to claim 6, wherein the suture retainer comprises any of a slot, shoulder and aperture.

8. A suture anchor assembly according to any of claim 1, wherein the anchoring element comprises means for distributing at least one stresses placed on the anchoring element by emplacement of the anchor assembly into the bone.

9. A suture anchor assembly according to claim 8, wherein the means for distributing stresses comprises an inner edge of at least one of the walls at a slot therein having at least one of a chamfer and a blend radius.

10. A suture anchor assembly according to claim 8, wherein the means for distributing stresses comprises a distal end of at least one of the axially-oriented slots that is at least one of radiused and rounded.

11. A suture anchor assembly according to claim 8, wherein the means for distributing stresses comprises inner edges of the walls at the slots therein having at least one of a chamfer and a blend radius, and distal ends of the axially-oriented slots being at least one of radiused and rounded.

12. A suture anchor assembly according to claim 8, wherein the means for distributing stresses comprises at least one of the axially-oriented slots being tapered.

13. A suture anchor assembly, comprising:
   an insertion stem having proximal and distal ends, the distal end for engagement with a distal end of a tubular anchoring element;
   a tubular anchoring element having defined therein an axial channel for loading onto the stem and having a distal end for engagement with the distal end of the stem, the anchoring element including inner and outer peripheral surfaces forming a wall therebetween, the wall having defined therein a plurality of axially-oriented slots in communication with the axial channel, the slots beginning at a proximal end of the element and extending distally, wherein the plurality of slots further define a plurality of flexible wall sections disposed between adjacent, axially-oriented slots;
   a tubular expander element having defined therein an axial channel, the expander element for loading onto the stem and having a distal end for engagement with the proximal end of the tubular anchoring element, wherein the tubular anchoring element is adapted for proximal movement within a bone hole from a first position, where a proximal end thereof is engaged with the distal end of the expander element, to a second position, where the proximal end of the tubular anchoring element cams over the distal end of the expander element so that flexible wall sections expand into a wall of the bone hole; and
   a suture retainer coupled to the insertion stem and disposed such that an under-tension suture therein places the suture retainer in compression.

14. A suture anchor assembly comprising:
an expander element having proximal and distal ends;
an anchoring element for movement within a bone hole from a first position, where a proximal end of the anchoring element is in facing relationship to the distal end of the expander element, and then to a second position, where the anchoring element moves within the bone hole so that the proximal end of the anchoring element cams over the distal end of the expander element, forcing the proximal end of the anchoring element into a wall of the bone hole;
the anchoring element including inner and outer peripheral surfaces forming a wall therebetween, the wall having defined therein a plurality of axially-oriented slots in communication with a axial channel, the slots beginning at a end of the element, wherein the plurality of slots further define a plurality of flexible wall sections disposed between adjacent, axially-oriented slots;
means for distributing at least one stresses placed on the anchoring element by emplacement of the anchor assembly into the bone.

15. A suture anchor assembly according to claim 14, wherein the means for distributing stresses comprises an inner edge of at least one of the walls at a slot therein having at least one of a chamfer and a blend radius.

16. A suture anchor assembly according to claim 14, wherein the means for distributing stresses comprises a distal end of at least one of the axially-oriented slots that is at least one of radiused and rounded.

17. A suture anchor assembly according to claim 14, wherein the means for distributing stresses comprises inner edges of the walls at the slots therein having at least one of a chamfer and a blend radius, and distal ends of the axially-oriented slots being at least one of radiused and rounded.

18. A suture anchor assembly according to claim 14, wherein the means for distributing stresses comprises at least one of the axially-oriented slots being tapered.

19. A suture anchor assembly comprising
a plurality of tubular anchoring elements, each having defined therein an axial channel for loading onto a common stem, the anchoring elements being arranged in series on that stem;
a distal-most anchoring element having a distal end for engagement with a proximal end of a distal end of the stem, each of the other anchoring elements having distal ends for engagement with a proximal end of an adjacent anchoring element;
each anchoring element including inner and outer peripheral surfaces forming a wall therebetween, the wall having defined therein a plurality of axially-oriented slots in communication with the axial channel, the slots beginning at a proximal end of the element and extending distally, wherein the plurality of slots further define a plurality of flexible wall sections disposed between adjacent, axially-oriented slots;
a tubular expander element having defined therein an axial channel, the expander element for loading onto the stem and having a distal end for engagement with a proximal end of a proximal-most anchoring element;
wherein the proximal-most anchoring element is adapted for proximal movement within a bone hole from a first position, where a proximal end thereof is engaged with the distal end of the expander element, to a second position, where the proximal end of that anchoring element cams over the distal end of the expander element so that flexible wall sections expand into a wall of the bone hole;
wherein the other anchoring elements are adapted for proximal movement within a bone hole from respective first positions, where their respective proximal ends are engaged with distal ends of respective adjacent anchoring elements, to respective second positions, where the respective proximal ends cam over respective distal ends so that the respective flexible wall sections expand into a wall of the bone hole;
a suture retainer coupled to the anchoring element and disposed such that an under-tension suture therein places the suture retainer in compression.

20. A suture anchor assembly according to any of claim 19 comprising a suture retainer coupled to a selected anchoring element and disposed such that an under-tension suture therein places the suture retainer in compression.

21. A suture anchor assembly according to any of claim 20, wherein the suture retainer is disposed at a distal end of the selected anchoring element.

22. A suture anchor assembly according to claim 21, wherein the suture retainer comprises a slot disposed at the distal end of the selected anchoring element.

23. A suture anchor assembly according to claim 22, wherein the suture retainer has a base that is rounded at the distal end of the selected anchoring element.

24. A suture anchor assembly according to claim 23, wherein the suture retainer has a base that is tear drop shaped.

25. A suture anchor assembly according to any of claim 20, wherein the suture retainer is disposed distal to a distal end of the axially-oriented slots defined in the walls of a selected anchoring element.

26. A suture anchor assembly according to claim 25, wherein the suture retainer comprises any of a slot, shoulder and aperture.

27. A suture anchor assembly according to any of claim 20, wherein at least a selected one of the anchoring elements includes means for distributing at lest one stresses placed thereon by emplacement of the anchor assembly into the bone.

28. A suture anchor assembly according to claim 27, wherein the means for distributing stresses comprises an inner edge of at least one of the walls at a slot therein having at least one of a chamfer and a blend radius.

29. A suture anchor assembly according to claim 27, wherein the means for distributing stresses comprises a distal end of at least one of the axially-oriented slots that is at least one of radiused and rounded.

30. A suture anchor assembly according to claim 27, wherein the means for distributing stresses comprises inner edges of the walls at the slots therein having at least one of a chamfer and a blend radius, and distal ends of the axially-oriented slots being at least one of radiused and rounded.

31. A suture anchor assembly according to claim 27, wherein the means for distributing stresses comprises at least one of the axially-oriented slots of the selected anchoring element being tapered.

32. A suture anchor assembly comprising:
an expander element having proximal and distal ends;
a plurality of anchoring elements, each having proximal and distal ends, and each for movement within a bone hole from (a) a first position, where a proximal end of the anchoring element is in facing relationship to the distal end of an adjacent one of the expander element and an anchoring element, to (b) a second position, where the anchoring element moves within the bone hole so that the proximal end of the anchoring element cams over the distal end of an adjacent one of the expander element and an anchoring element, forcing the proximal end of the anchoring element into a wall of the bone hole;

the anchoring elements each including inner and outer peripheral surfaces forming a wall therebetween, the wall having defined therein a plurality of axially-oriented slots in communication with a axial channel, the slots beginning at a end of the element, wherein the plurality of slots further define a plurality of flexible wall sections disposed between adjacent, axially-oriented slots.

\* \* \* \* \*